US010993778B2

(12) United States Patent
Bellows et al.

(10) Patent No.: US 10,993,778 B2
(45) Date of Patent: May 4, 2021

(54) BRAKE ACTUATOR FOR MEDICAL DEVICE SUPPORT SYSTEM

(71) Applicant: American Sterilizer Company, Mentor, OH (US)

(72) Inventors: Lance Clark Bellows, Painesville, OH (US); Christopher Roy Mohr, Mentor, OH (US)

(73) Assignee: American Sterilizer Company, Mentor, OH (US)

( * ) Notice: Subject to any disclaimer, the term of this patent is extended or adjusted under 35 U.S.C. 154(b) by 155 days.

(21) Appl. No.: 16/517,707

(22) Filed: Jul. 22, 2019

(65) Prior Publication Data

US 2020/0030057 A1 Jan. 30, 2020

Related U.S. Application Data

(60) Provisional application No. 62/702,943, filed on Jul. 25, 2018, provisional application No. 62/702,946, (Continued)

(51) Int. Cl.
*A61B 90/50* (2016.01)
*F16M 11/20* (2006.01)
(Continued)

(52) U.S. Cl.
CPC ............ *A61B 90/50* (2016.02); *F16D 65/065* (2013.01); *F16D 65/14* (2013.01);
(Continued)

(58) Field of Classification Search
CPC . A61B 90/50; A61B 2090/508; F16D 65/065; F16D 65/14; F16D 2121/14; F16M 11/2014
See application file for complete search history.

(56) References Cited

U.S. PATENT DOCUMENTS 632,187 A 8/1899 Joyce
3,866,722 A * 2/1975 Kjos ...................... F16D 63/00
188/75
(Continued)

FOREIGN PATENT DOCUMENTS

DE 20218693 U1 2/2003
DE 102016005785 A1 11/2017
(Continued)

OTHER PUBLICATIONS

International Search Report and Written Opinion of the International Searching Authority; Application No. PCT/US2019/042736, dated Oct. 11, 2019.

*Primary Examiner* — Anita M King
(74) *Attorney, Agent, or Firm* — Renner, Otto, Boisselle & Sklar, LLP

(57) ABSTRACT

A medical device support system including a central shaft, an extension arm, a brake clamp assembly, and a brake actuator. The extension arm has a support for a medical device and a hub at its proximal end mounted to the central shaft for pivotable movement about the central shaft. The brake clamp assembly is secured in the hub for rotation therewith and includes first and second clamp portions. The brake actuator includes a cap, a plunger coupled to the cap for reciprocable axial movement relative to the cap, and a spring disposed between the cap and the plunger and configured to exert a biasing force against movement of the cap axially toward the plunger. The cap is adjustably mounted to the hub and coupled to the plunger to selectively urge the first and second clamp portions either toward or away from the central shaft to respectively increase or decrease a frictional braking force to the central shaft.

23 Claims, 9 Drawing Sheets

Related U.S. Application Data filed on Jul. 25, 2018, provisional application No. 62/702,947, filed on Jul. 25, 2018, provisional application No. 62/702,948, filed on Jul. 25, 2018, provisional application No. 62/799,096, filed on Jan. 31, 2019, provisional application No. 62/799,100, filed on Jan. 31, 2019, provisional application No. 62/799,113, filed on Jan. 31, 2019, provisional application No. 62/799,202, filed on Jan. 31, 2019, provisional application No. 62/809,173, filed on Feb. 22, 2019, provisional application No. 62/825,078, filed on Mar. 28, 2019, provisional application No. 62/828,090, filed on Apr. 2, 2019.

(51) Int. Cl.
*F16D 65/14* (2006.01)
*F16D 65/06* (2006.01)
*F16D 121/14* (2012.01)

(52) U.S. Cl.
CPC .... *F16M 11/2014* (2013.01); *A61B 2090/508* (2016.02); *F16D 2121/14* (2013.01)

(56) References Cited

U.S. PATENT DOCUMENTS

| | | | |
|---|---|---|---|
| 4,200,407 A | 4/1980 | Bianco | |
| RE32,214 E * | 7/1986 | Schramm | A61M 5/31595 604/232 |
| 5,851,095 A | 12/1998 | Ellis et al. | |
| 6,899,442 B2 * | 5/2005 | Howell | E04B 9/006 248/278.1 |
| 7,097,145 B2 * | 8/2006 | Turner | F16M 11/10 248/274.1 |
| 8,888,696 B2 * | 11/2014 | Marka | A61B 90/30 600/249 |
| 9,103,178 B2 * | 8/2015 | Beach | E21B 31/20 |
| 10,335,961 B2 * | 7/2019 | Christiansen | A61B 34/70 |
| 10,591,006 B2 * | 3/2020 | Puterbaugh | F16M 13/027 |
| 10,760,611 B2 * | 9/2020 | Oginski | F16M 11/2014 |
| 10,767,811 B2 * | 9/2020 | Timoszyk | F21V 21/26 |
| 10,835,346 B2 * | 11/2020 | Bellows | F16D 65/14 |
| 10,874,476 B2 * | 12/2020 | Bellows | F16M 11/08 |
| 2004/0104328 A1 | 6/2004 | Frick | |
| 2012/0099943 A1 | 4/2012 | Chiu | |
| 2015/0184779 A1 * | 7/2015 | Timoszyk | A61B 90/30 285/282 |
| 2015/0292538 A1 | 10/2015 | He | |
| 2017/0079743 A1 | 3/2017 | Tao | |
| 2017/0326738 A1 | 11/2017 | Christiansen et al. | |

FOREIGN PATENT DOCUMENTS

| | | |
|---|---|---|
| EP | 1239805 A1 | 9/2002 |
| FR | 1441338 A | 6/1966 |
| WO | 0145627 A1 | 6/2001 |

* cited by examiner

BRAKE ACTUATOR FOR MEDICAL DEVICE SUPPORT SYSTEM

This application claims priority to U.S. Patent Application No. 62/702,943 filed Jul. 25, 2018; U.S. Patent Application No. 62/702,946 filed Jul. 25, 2018; U.S. Patent Application No. 62/702,947 filed Jul. 25, 2018; U.S. Patent Application No. 62/702,948 filed Jul. 25, 2018; U.S. Patent Application No. 62/799,096 filed Jan. 31, 2019; U.S. Patent Application No. 62/799,100 filed Jan. 31, 2019; U.S. Patent Application No. 62/799,113 filed Jan. 31, 2019; U.S. Patent Application No. 62/799,202 filed Jan. 31, 2019; U.S. Patent Application No. 62/809,173 filed Feb. 22, 2019; U.S. Patent Application No. 62/825,078 filed Mar. 28, 2019; and U.S. Patent Application No. 62/828,090 filed Apr. 2, 2019. These prior applications are incorporated herein by reference.

FIELD OF INVENTION

This application relates generally to a brake actuator for a medical device suspension system or carry system for use in, for example, a hospital examination room, a clinic, a surgery room or an emergency room, and more particularly to a brake actuator that has a self-contained structure that simplifies assembly and field service.

BACKGROUND

Medical device suspension systems or carry systems are used in health treatment settings such as hospital examination rooms, clinics, surgery rooms and emergency rooms. These systems may suspend or support any variety of medical devices or components including surgical lights, supply consoles, patient monitors, camera detector heads, medical instruments, ventilator systems, suction devices, among others. The supports typically include a central shaft or support column that is suspended from the ceiling or mounted to a wall, and one or more generally horizontal extension arms mounted for rotational movement about the shaft. A frictional brake is provided near the pivot location of the extension arm that is operable to maintain the extension arm in the desired angular position and to permit angular adjustment by a suitable force against the extension arm. The extension arm can be rotatably adjusted about the column to a desired angular position to provide appropriate access to medical devices and components associated with the arm.

Most of the current support systems utilize mechanical radial braking devices to provide the required rotational performances of system components. The basic principle of these devices is that the force needed to achieve the desired level of frictional braking is applied in the radial direction, transverse or perpendicular to the axis of component rotation. One example is a clamp assembly that has a generally C-shape construction. The clamp assembly is installed over the central shaft and into a hub portion of the pivoting extension arm. An actuator, which may also be part of the hub, is used to urge the opposite sides of the brake clamp toward and away from the shaft. This process creates a normal force between the brake clamp and the shaft, and provides necessary frictional force to control the pivotable movement of the arm around the shaft.

For some medical device suspension systems or carry systems, there remain various shortcomings, drawbacks, and disadvantages relative to certain applications. For example, in some C-shape brake clamp type assemblies, the brake actuator may include a set screw, plunger, and spring which, together in conjunction with the hub wall, apply a spring biased compression force against opposing tabs of the clamp. In some applications, a rod portion of the plunger has to be inserted into a hole in one of the opposing tabs, the spring has to be positioned on the plunger rod, and the set screw has to be positioned to press against the back of the plunger. Because the set screw, plunger and spring are separate components, the actuator has to be assembled along with and at the same time as the shaft and hub. A problem arises in that the actuator cannot be removed and replaced after the suspension system is assembled without disassembling the hub portion of the extension arm from the shaft. Moreover, because the set screw, plunger and spring are separate components, each has to be individually held, positioned, and aligned in a particular manner and sequence relative to one another and relative to the hub wall and the clamp assembly to achieve proper assembly and functioning of the brake actuator. The handling, positioning and aligning of the components may be complicated further by tight clearances between the brake clamp assembly and the hub wall. This can result in incorrectly assembled or misaligned components and unnecessary expenditure of time.

Accordingly, there remains a need for further contributions in this area of technology.

SUMMARY OF INVENTION

The application relates to a brake actuator for a medical device support system, in which the brake actuator includes a cap, a spring and a plunger coupled together in a self-contained manner. The brake actuator simplifies assembly and field service since the components need not be separately handled and positioned and/or aligned relative to one another in adjustably mounting the brake actuator in the hub.

According to one aspect of the invention, a medical device support system includes a central shaft, an extension arm, a brake clamp assembly, and a brake actuator. The extension arm has a support for a medical device and a hub at its proximal end mounted to the central shaft for pivotable movement about the central shaft. The brake clamp assembly is secured in the hub for rotation therewith and includes first and second clamp portions. The brake actuator includes a cap, a plunger coupled to the cap for reciprocable axial movement relative to the cap, and a spring disposed between the cap and the plunger and configured to exert a biasing force against movement of the cap axially toward the plunger. The cap is adjustably mounted to the hub and coupled to the plunger to selectively urge the first and second clamp portions either toward or away from the central shaft to respectively increase or decrease a frictional braking force to the central shaft.

Embodiments of the invention may include one or more of the following additional features separately or in combination.

The plunger may be coupled to the cap to prevent separation of the plunger from the cap.

The cap may be configured to compress the spring against a head of the plunger, and the head of the plunger may, in turn, urge the first and second clamp portions toward the central shaft to increase the frictional braking force to the central shaft.

The cap may threadably engage a threaded opening in the hub.

The minor diameter of the threaded opening in the hub may be greater than a maximum width of the plunger in axial cross section and a maximum width of the spring in axial cross section.

The brake clamp assembly may be configured to operate in a passive manner, preventing motion of the extension arm relative to the central shaft by means of the frictional braking force, wherein the frictional braking force can be overcome by a user pushing on the extension arm.

The first and second clamp portions may form a split collar around the central shaft, and the free ends of the clamp portions may include respective tabs that protrude radially outwardly relative to the central shaft. The cap may be adjustably mounted to the hub and coupled to the plunger to exert a force on the plunger against one of the tabs to apply a compressive force to the tabs to urge the first and second clamp portions toward one another thereby to impart the frictional braking force to the central shaft.

A head of the plunger may exert the force against the one of the tabs, and the one of the tabs may be slidable relative to the head in a direction axially and radially relative to the central shaft.

The medical device may be a surgical light.

The brake clamp assembly may include brake liners made of a material selected from polyolefins, polyesters, acetals, polyamides, fluorinated polymers, vinyls, acrylics, polycarbonates, polyimides, polysulphones, and blends and alloys thereof.

The brake clamp assembly may include brake liners made of a material including unreinforced, semi-crystalline thermoplastic polyester based on polyethylene terephthalate (PET-P).

The brake clamp assembly includes brake liners made of a material including UHMW-PE.

According to another aspect of the invention, a brake actuator for a medical device support system may include a plunger, a cap and a spring. The plunger may include a rod, a head at one axial end of the rod, and a stop flange at an opposite axial end of the rod. The cap may include a body, a mating coupling at one axial end of the body, and a driving end at an opposite axial end of the body. The mating coupling may be coupled to the rod for reciprocable axial movement relative to the rod toward and away from the head. The stop flange may be configured to abut an interior portion of the mating coupling to prevent separation of the plunger from the cap. The spring may be disposed between the mating coupling and the head, and be configured to exert a biasing force against movement of the cap axially toward the head.

Embodiments of the invention may include one or more of the following additional features separately or in combination.

The cap may be externally threaded and have a minor diameter that is greater than a maximum width of the head in axial cross section and a maximum width of the spring in axial cross section.

The opposite axial end of the rod may have a hollow rod end, and the stop flange may be formed as a flared end of the hollow rod end.

The cap may have a central opening that slidably receives the rod to guide the reciprocable axial movement.

The stop flange may project radially outward from the rod, and the interior portion of the mating coupling may include a ledge that projects radially outward from the central opening. The stop flange may abut the ledge to prevent separation of the plunger from the cap.

The stop flange may be annular in shape and the radially outward projecting ledge may be annular in shape.

The inner diameter of the spring may be slightly larger than an outer diameter of the rod.

The spring may include a plurality of Belleville washers.

The cap may be externally threaded and the driving end of the cap may include a tool fitting for mating with a tool from which the cap can be driven axially by threadably engaging a threaded opening in a hub of the medical device support system.

According to another aspect of the invention, there is provided a method of adjusting a brake assembly of a medical device support system having a central shaft, an extension arm having a support for a medical device and a hub at its proximal end mounted to the central shaft for pivotable movement about the central shaft, and a brake clamp assembly secured in the hub for rotation therewith and including first and second clamp portions. The method may include providing a brake actuator including a cap, a plunger coupled to the cap for reciprocable axial movement relative to the cap, and a spring disposed between the cap and the plunger to exert a biasing force against movement of the cap axially toward the plunger, adjustably mounting the cap into an opening in the hub and coupling the cap to the plunger to urge the first and second clamp portions toward the central shaft to increase a frictional braking force to the central shaft, wherein as the cap is adjustably mounted into the opening the cap, against the biasing force of the spring, urges the spring against a head of the plunger, and the head of the plunger, in turn, urges the first and second clamp portions toward the central shaft to increase a frictional braking force to the central shaft. As the cap is mounted into the opening the cap may push the plunger, and the spring disposed between the plunger and the cap, through the opening as a self-contained assembly.

Embodiments of the invention may include one or more of the following additional features separately or in combination.

The method may include removing the cap from the opening in the hub. As the cap is removed the cap may pull the plunger, and the spring disposed between the plunger and the cap, through the opening as a self-contained assembly.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention.

DETAILED DESCRIPTION

Figure 1:
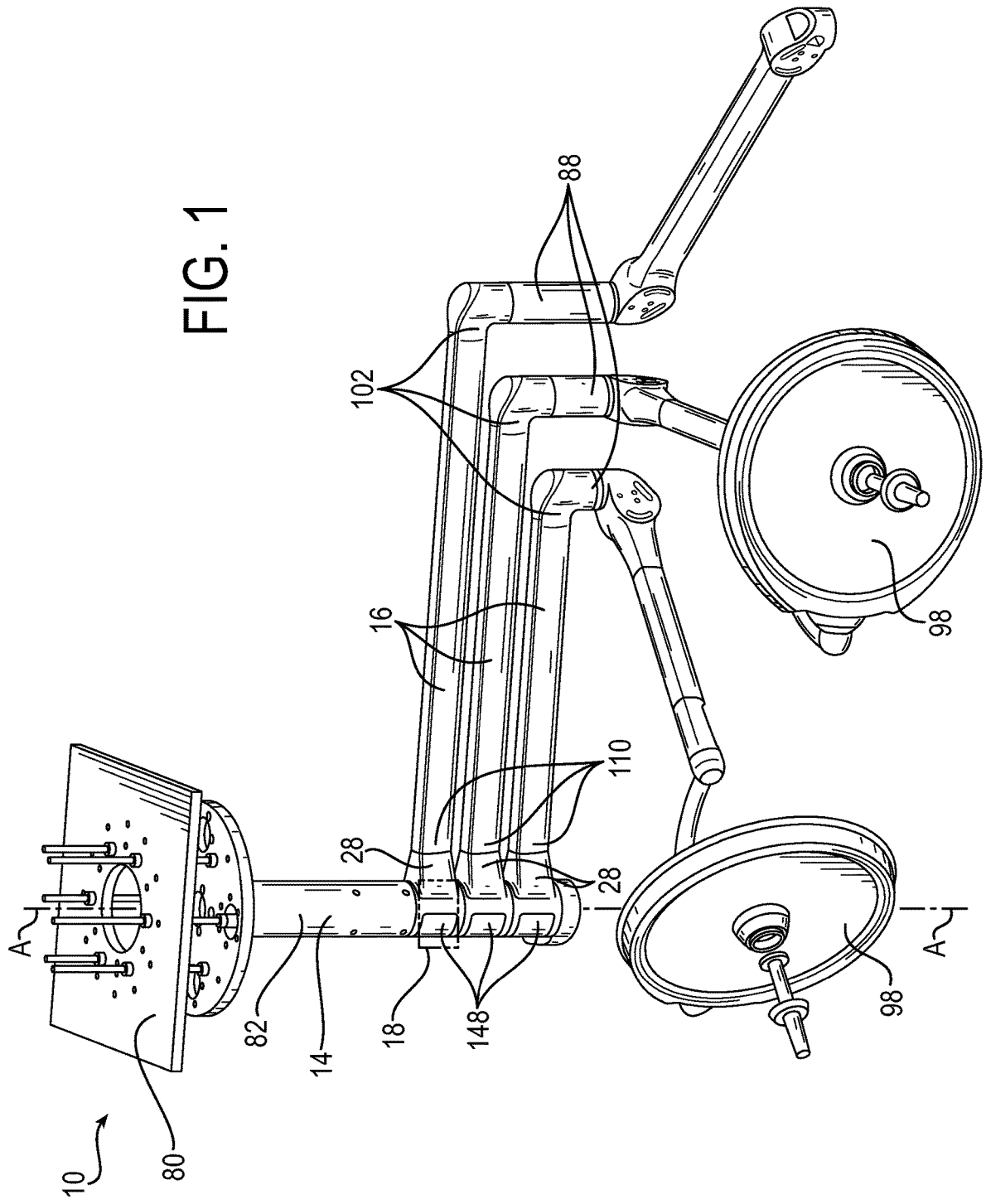
FIG. 1 is a perspective view of a medical device support system in accordance with an embodiment of the invention.

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments, and any further applications of the principles of the invention as described herein, are contemplated as would normally occur to one skilled in the art to which the invention relates.

Figure 2:
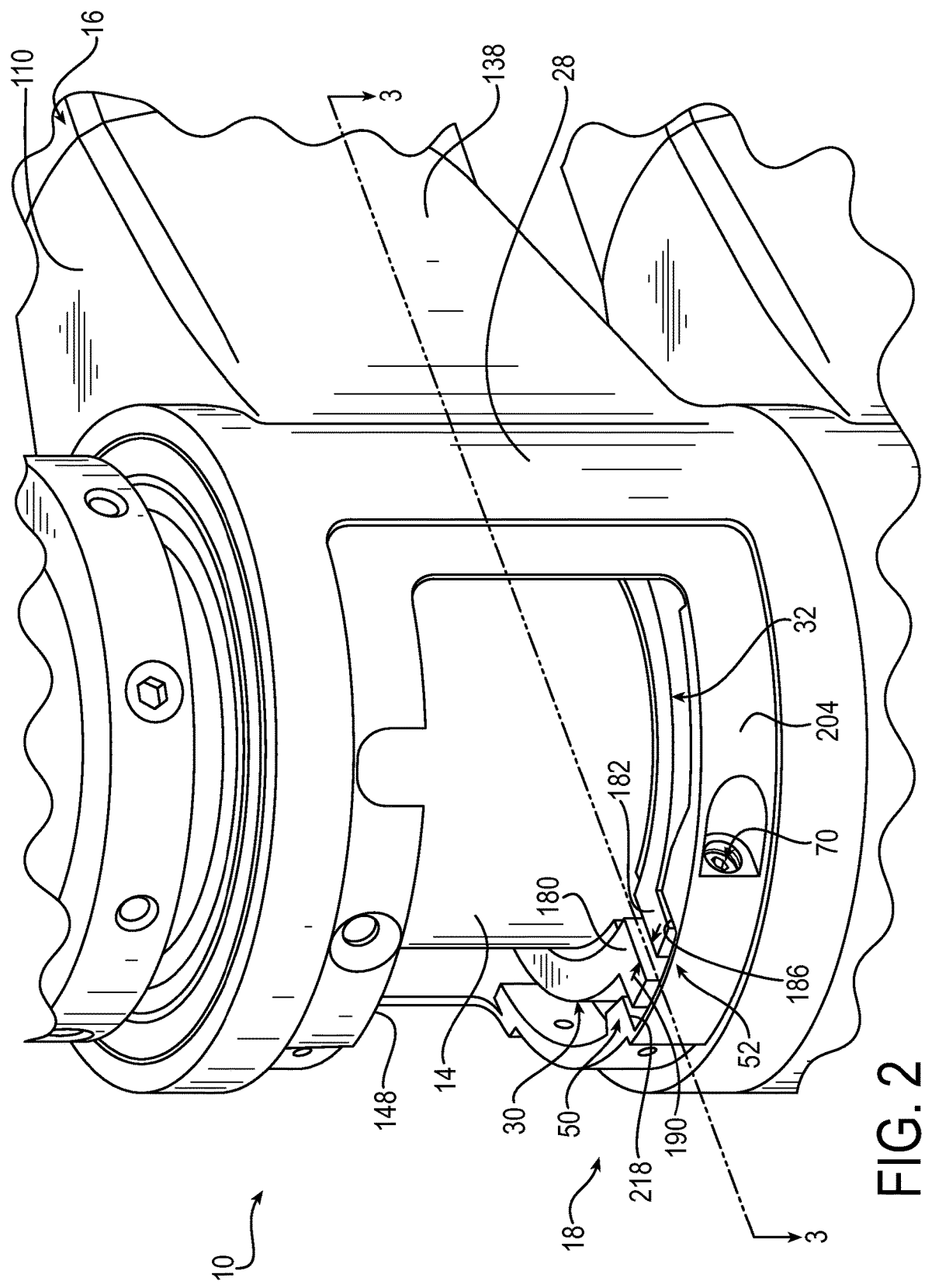
FIG. 2 is a perspective view of a portion of the medical device support system of FIG. 1, showing an example brake actuator and brake clamp assembly of the system.
Figure 3:
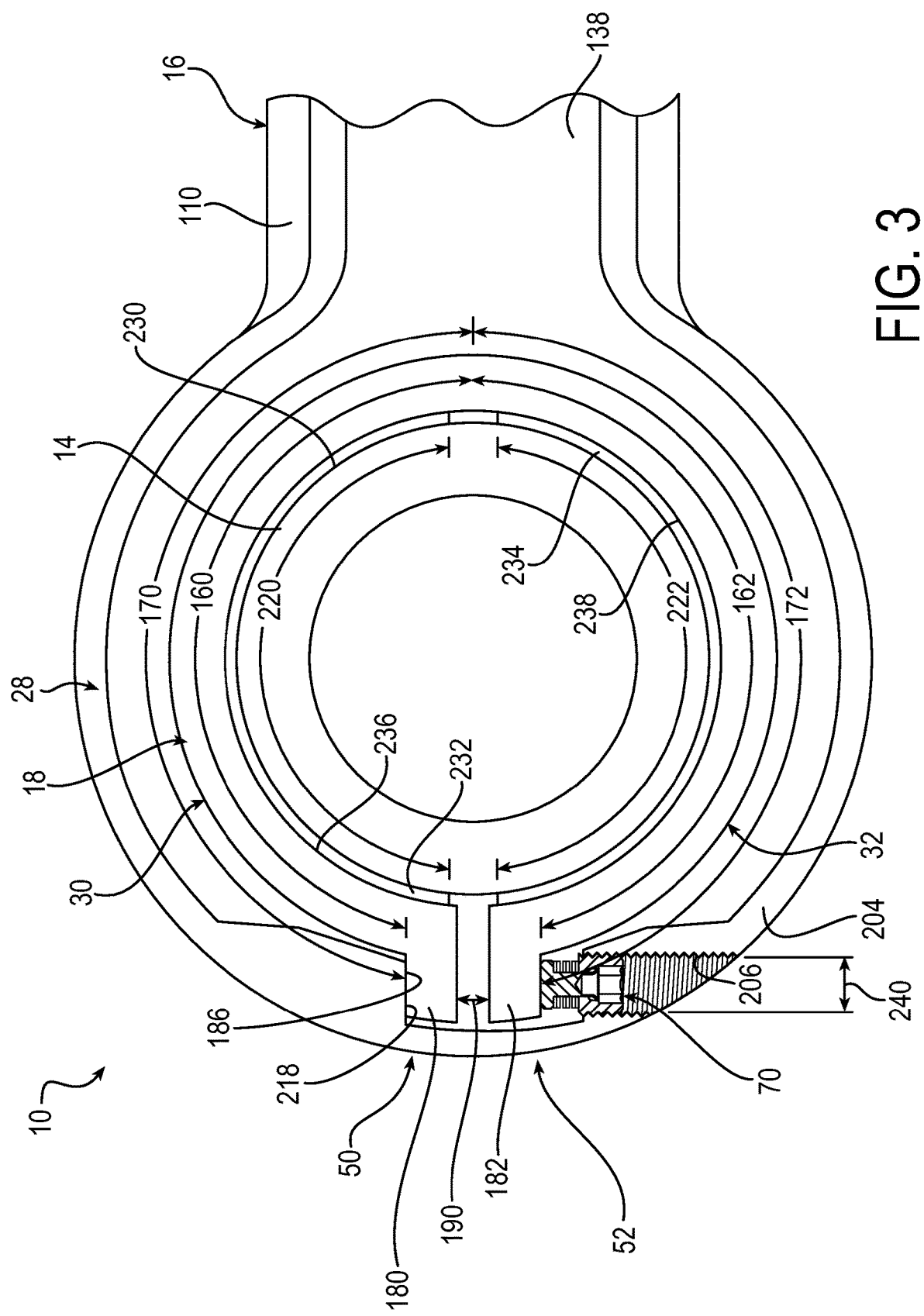
FIG. 3 is a cross-section view of the FIG. 2 portion of the medical device support system as viewed from the plane 3-3 in FIG. 2.

FIGS. 1-3 show a medical device support system 10 that includes a central shaft 14, at least one extension arm 16 rotatably mounted to the shaft 14, a brake clamp assembly 18, and a brake actuator 70. The brake clamp assembly 18 is secured in a hub 28 of the extension arm 16 for rotation with the extension arm 16. As shown in FIGS. 2 and 3, the brake clamp assembly 18 is of the split clamp type and includes first and second clamp portions 30, 32 that are free to move at their respective distal ends 50, 52. The brake actuator 70 includes a cap 90, a plunger 92, and a spring 94 coupled together as a self-contained assembly. The plunger 92 is coupled to the cap 90 for reciprocable axial movement relative to the cap 90. The spring 94 is disposed between the cap 90 and the plunger 92 and configured to exert a biasing force against movement of the cap 90 axially toward the plunger 92. The cap 90 is adjustably mounted to the hub 28 and coupled to the plunger 92 to selectively urge the first and second clamp portions 30, 32 either toward or away from the central shaft 14 to respectively increase or decrease a frictional braking force to the central shaft 14. As will be described in greater detail below, the brake actuator 70 simplifies assembly and field service since the components thereof need not be separately handled and positioned and/or aligned relative to one another in adjustably mounting the brake actuator 70 in the hub 28.

Referring to FIG. 1, the illustrative medical device support system 10 is a suspension type carrying support system for use in a hospital examination room, a clinic, a surgery room, an emergency room, among others. The central shaft 14 extends along an axis A-A. The central shaft 14 may be fixed to a ceiling support 80 to remain stationary relative to the ceiling. It will be appreciated, of course, that the medical device support system 10 may have any suitable suspension or carrying structure and that the central shaft 14 may be attached to a ceiling, wall, floor, movable cart, or a combination of the foregoing. The central shaft 14 of the medical device support system 10 has a circular shape in axial cross section and extends vertically downward from the ceiling support 80. A column section 82 surrounds an upper portion of the central shaft 14 and houses upper portions of accessory and service lines such as power cables for surgical lights and other power requirements, control wiring for control electronics, and/or tubing for irrigation, suction, etc. A plurality of extension arms 16, three in the illustrative embodiment, are mounted for rotatable movement to the central shaft 14 and extend laterally outward from the central shaft 14. In the FIG. 1 embodiment, the extension arms 16 extend horizontally, or perpendicularly, relative to the central shaft 14.

Each extension arm 16 is equipped with a support 88 for a medical device 98. The illustrative support 88 is a vertical column 88 extending downward from a distal end 102 of the horizontal extension arm 16. The vertical column 88 may be mounted for rotatable movement to the distal end 102 of the extension arm 16 by means of a bearing, and may be equipped to frictionally engage the distal end 102, for example, by means of a brake clamp assembly 18 in the same manner that the extension arm 16 is rotatably mounted and braked relative to the central shaft 14. In the FIG. 1 embodiment, the medical device 98 comprises a surgical light 98 attached to a bottom end of the vertical column 88. Of course, the medical device support system 10 need not be limited as such and other embodiments are contemplated. For example, the medical device 98 may comprise a patient monitor, a supply console, a camera detector head, a medical instrument, a ventilator system, a suction device, among others. A control console, if provided, may provide controls for navigation of a medical instrument that is either coupled to or remote from the extension arm 16.

The hub 28 is located at the proximal end 110 of the extension arm 16 and is mounted to the central shaft 14 for pivotable movement about the central shaft 14. In the illustrative embodiment, each hub 28 includes upper and lower bearing mounts that house respective upper and lower pivot bearings mounted to the central shaft 14. Any suitable pivot bearings may be used to facilitate the relative rotational movement between the extension arm 16 and the central shaft 14, including for example ball bearings, sleeve bearings, bushings, rotary joints and/or swivel joints. Each hub 28 provides passages for routing accessory and service lines from the upper column section 82 to the radial extent 138 of the extension arm 16 and/or vice versa. Each hub 28 is also provided with an access opening 148 to enable access to the central shaft 14, the brake clamp assembly 18, and the accessory and service lines.

Figure 5:
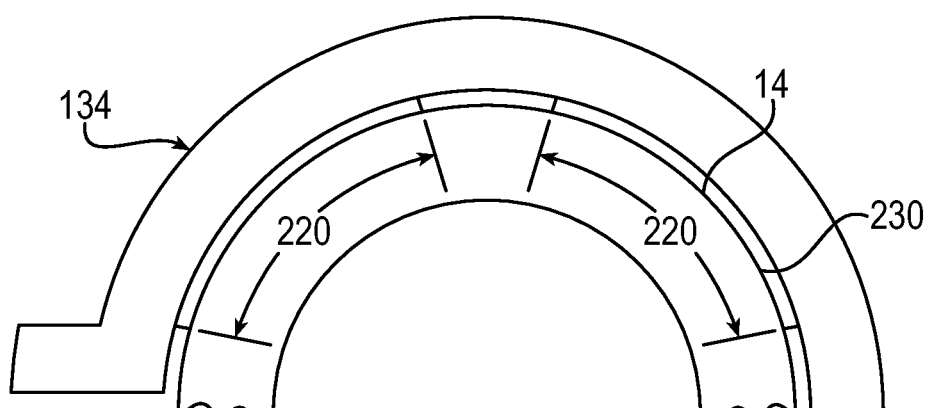
FIG. 5 is a top view of view an arc shape clamp piece of a brake assembly in accordance with another embodiment of the invention.
Figure 6:
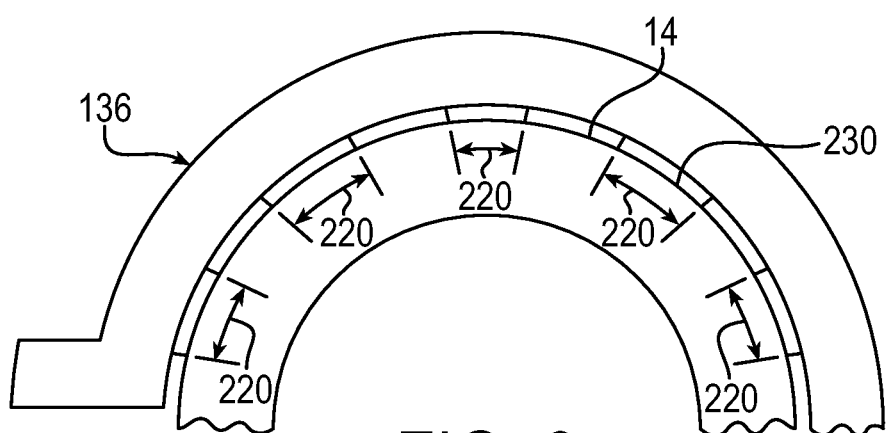
FIG. 6 is a top view of view an arc shape clamp piece of a brake assembly in accordance with another embodiment of the invention.
Figure 7:
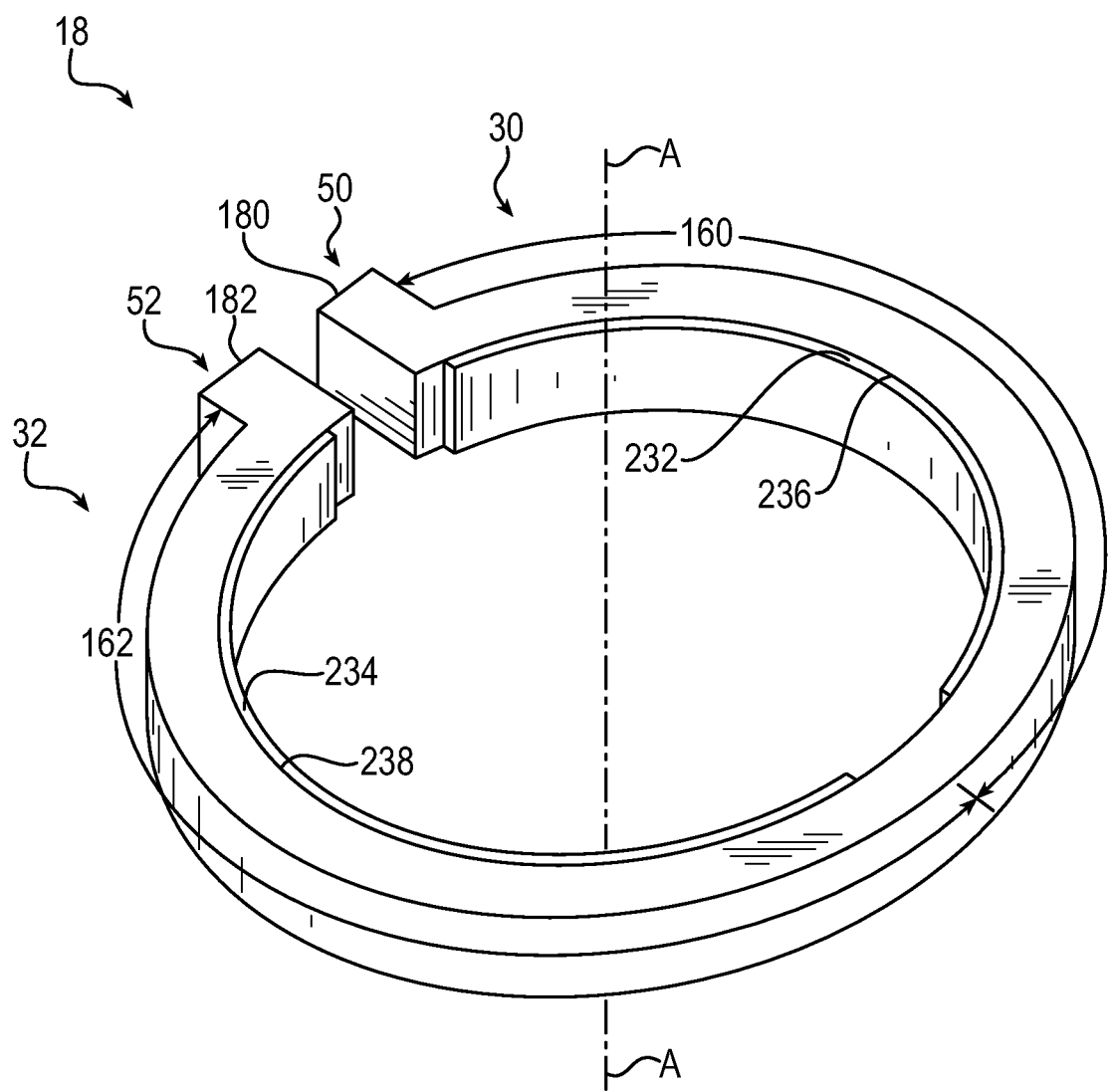
FIG. 7 shows greater detail of a brake clamp assembly in accordance with an embodiment of the invention.

Reference is now made to FIGS. 2-11 which show greater detail of the brake clamp assembly 18 and the brake actuator 70. The brake clamp assembly 18 is secured in the hub 28 for rotation with the hub 28. As shown in FIG. 7, the brake clamp assembly 18 includes first and second clamp portions 30, 32 that are fixed to one another at one end for flexural movement while being free to move at an opposite end 50, 52, to allow flexural movement of the clamp portions 30, 32 toward and away from one each other. In the illustrative embodiment, each of the clamp portions 30, 32 of the brake clamp assembly 18 has a circumferential portion 160, 162 and the free end 50, 52 at respective distal ends of the circumferential portions 160, 162. As shown in FIG. 3, the clamp portions 30, 32 form a split collar or ring wherein the circumferential portions 160, 162 form the ring portion thereof, and a gap between the free ends 50, 52 forms the split thereof. The circumferential portions 160, 162 are sized to fit within and radially inward of inner circumferential portions 170, 172 of the hub 28. The clamp portions 30, 32 may rest by means of gravity directly on a lower bearing mount. A retaining snap ring may be mounted in a groove in the central shaft 14 immediately above, or a slight clearance above, the clamp portions 30, 32 and/or immediately below, or a slight clearance below, the clamp portions 30, 32 to axially retain or guide the clamp portions 30, 32 relative to the central shaft 14.

The free ends 50, 52 of the clamp portions 30, 32 include tabs 180, 182 that protrude radially outwardly relative to the circumferential portions 160, 162. As shown in FIGS. 2 and 3, the radially protruding tabs 180, 182 fit within a radially protruding notch 186 in the hub 28, which notch 186 is disposed circumferentially between the inner circumferential portions 170, 172 of the hub 28. The tabs 180, 182, when installed in the hub notch 186, circumferentially oppose one another and form a circumferential gap therebetween referred to herein as a deflection compensation split 190.

Figure 8:
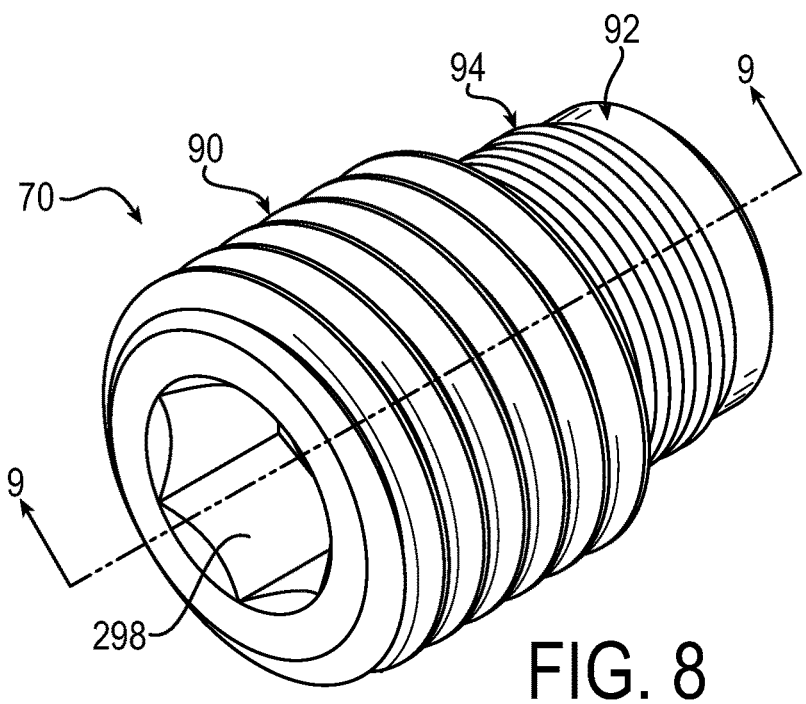
FIG. 8 is a perspective view of a brake actuator in accordance with an embodiment of the invention.

The brake actuator 70 actuates the brake clamp assembly 18. The brake actuator 70 is a self-contained assembly that includes the cap 90, the plunger 92, and the spring 94 disposed between the cap 90 and the plunger 92. The plunger 92 is coupled to the cap 90 for reciprocable axial movement relative to the cap 90, for example along the axis B-B in FIG. 8. Further, the plunger 92 is coupled to the cap 90 to prevent separation of the plunger 92 from the cap 90. As shown in FIG. 8, for example, and as will be described in greater detail below, this separation prevention coupling can be by means of a stop flange 200 of the plunger 92 axially abutting an interior portion 202 of the cap 90. The spring 94 is configured to exert a biasing force against movement of the cap 90 axially toward the plunger 92, as is also shown in FIG. 8.

As shown in FIGS. 2 and 3, the brake actuator 70 is housed in a wall portion 204 of the hub 28. The cap 90 is adjustably mounted to the hub 28, as by threadably engaging a threaded opening 206 in the hub 28, and coupled to the plunger 92 to selectively urge the first and second clamp portions 30, 32 either toward or away from the central shaft 14 to respectively increase or decrease a frictional braking force to the central shaft 14.

The brake actuator 70 is operative selectively to apply a compressive force to the tabs 180, 182 to urge the first and second clamp portions 30, 32 toward one another thereby to impart a frictional braking force to the central shaft 14. The cap 90 is coupled to the plunger 92 to exert a force on the plunger 92 against one of the tabs, tab 182 in the illustrative embodiment, to apply a compressive force to the tabs 180, 182 to urge the first and second clamp portions 30, 32 toward one another thereby to impart the frictional braking force to the central shaft 14. As shown in FIG. 3, the plunger 92 is configured to apply a load to the rear of the tab 182. When the cap 90 is threaded inward into the wall portion 204 of the hub 28, the cap 90 presses against the rear of the spring 94, and the front of the spring 94 presses against the plunger 92, which in turn presses against the tab 182, which compresses the tab 182 toward the opposite tab 180. The opposite tab 180 provides resistance to the compressive force applied by the brake actuator 70 by resting against a wall 218 of the notch 186 in the hub 28. In so doing, the cap 90 is configured to compress the spring 94 against a head 208 of the plunger 92, and the head 208 of the plunger 92, in turn, urges the first and second clamp portions 30, 32 toward the central shaft 14 to increase the frictional braking force to the central shaft 14.

In operation, tightening the cap 90 of the brake actuator 70 compresses the tabs 180, 182 and thereby narrows the deflection compensation split 190 and flexes the first and second clamp portions 30, 32 toward one another and toward the central shaft 14. Loosening the cap 90 causes the tabs 180, 182 to separate from one another owing to the resistive force imparted by the notch wall 218 of the hub 28 against the rear of the tab 180, which results in the deflection compensation split 190 expanding and the first and second clamp portions 30, 32 unflexing away from one another and away from the central shaft 14. Thus, the deflection compensation split 190 between the free ends 50, 52 compensates for deflection caused by the application of compressive force on the tabs 180, 182, which creates a tangential frictional force that supplies the braking relative to the central shaft 14. The brake actuator 70 is configured to increase increase and decrease the frictional braking force applied by the brake clamp assembly 18 to the central shaft 14 to respectively increase and decrease the resistance to pivotable movement of the extension arm 16 about the central shaft 14. The brake actuator 70 and brake clamp assembly 18 are configured to operate in a passive manner, preventing motion of the extension arm 16 relative to the central shaft 14 by means of an "always-on" frictional braking force that can be overcome by a user pushing on the extension arm 16. The amount of frictional resistance can be adjusted as desired by the user by adjusting the brake actuator 70. The brake actuator 70 can be used to adjust the frictional resistance as suited for a particular physician and/or on a periodic basis to ensure the previously set frictional resistance still is in place and not loosened over time.

It will be appreciated that a suitable actuator can be employed to generate a lock mode, a frictional resistance mode, and/or a release mode. For example, the actuator can be configured to adjust the brake clamp assembly 18 to generate a braking force, whether by friction or an interengaging mechanism such as a cam lock or piston lock, sufficient to lock the extension arm 16 to the central shaft 14, and/or to generate a frictional braking force that prevents rotation of the extension arm 16 about the central shaft 14 yet enables a user to overcome the resistance by pushing the extension arm 16 about the central shaft 14, and/or to generate a relatively lower or zero frictional braking force sufficient to free or release the extension arm 16 for pivotable movement about the central shaft 14 with relatively less or negligible force by the user. It will further be appreciated that the brake clamp assembly 18 could be adapted for an active braking system, one which provides an active braking functionality that can apply a frictional braking force actively, for example, by means of electromagnetic actuation, pneumatic actuation, or hydraulic actuation.

The first and second clamp portions 30, 32 are disposed around the central shaft 14 and are configured to contract and expand relative to the central shaft 14 in response to the flexural movement of the first and second clamp portions toward and away from one another and toward and away from the shaft 14. As will be appreciated, as the first and second clamp portions 30, 32 of the brake clamp assembly 18 are flexed toward and away from one another, the circumferential portions 160, 162 and free ends 50, 52 of the clamp portions 30, 32 move closer together and farther apart to respectively contract and expand the split collar. As shown in FIG. 3, when the first and second clamp portions 30, 32 are flexed toward each other to increase the frictional braking force applied to the central shaft 14, the first and second clamp portions 30, 32 each have an angular range or arc shape contact 220, 222 with the outer periphery 230 of the central shaft 14 of about 165 degrees, or a total of about 330 degrees. Although the illustrative first and second clamp portions 30, 32 are diametrically opposed from one another on opposite sides of the central shaft 14, it will be appreciated that the clamp portions 30, 32 may be other than diametrically opposed.

Figure 4:
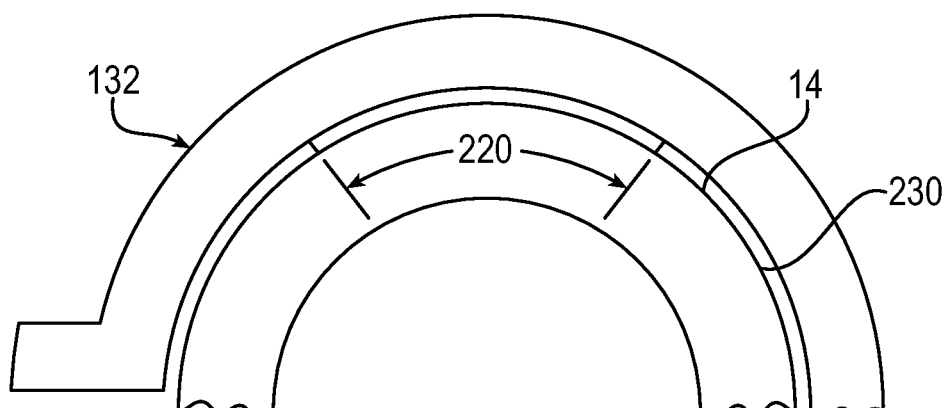
FIG. 4 is a top view of view an arc shape clamp piece of a brake assembly in accordance with an embodiment of the invention.

It will also be appreciated that the angular range contact of the clamp portions 30, 32 may be other than 165 degrees, and thus other than a total of 330 degrees. For example, FIG. 4 shows an alternate embodiment of an arc shape clamp portion 132 for which the angular range contact with the central shaft 14 is about 30 degrees, thus totaling a 60 degree angular range contact in the case where opposing arc shape clamp portions 132 have the same angular range contact. FIG. 5 shows another embodiment in which the arc shape clamp portion 134 has two angular range contacts, one each of about 30 degrees, thus totaling a 120 degree angular range contact in the case where opposing arc shape clamp portions 134 have the same angular range contact. FIG. 6 shows yet another embodiment of an arc shape clamp portion 136. Here, the arc shape clamp portion 136 has five angular range contacts, one each of about 15 degrees, thus totaling a 150 degree angular range contact in the case where opposing arc shape clamp portions 136 have the same angular range contact. Still other embodiments may have other angular range contacts. It will be understood that opposing arc shape clamp portions need not have the same angular range contacts, whether in the quantity or size of the arc shape clamp portions, or the components that form the arc shape clamp portions.

FIG. 7 shows greater detail of the brake clamp assembly 18. The first and second clamp portions 30, 32 include arc shape backing portions made up of the circumferential portions 160, 162 and radially protruding tabs 180, 182, and respective polymer liners 232, 234 mounted to radially inner walls 236, 238 of the circumferential portions 160, 162, for example by adhesive bonding. In the illustrative embodiment, the polymer liners 232, 234 have identical geometries; that is, the polymer liners 232, 234 have a one part geometry. The identical geometries eliminate the need for extra unique component designs. It will be appreciated that the liners 232, 234 may have different geometries, or components thereof may have some identical geometries and some different geometries.

The arc shape backing portions 160, 162, 180, 182 may be made of any suitable materials, for example, metal or metal alloy. The arc shape backing portions 160, 162, 180, 182 may be made by means of casting, machining, powdered metallurgy and/or metal injection molding. In some applications, the arc shape backing portions 160, 162, 180, 182 may be made by means of additive manufacturing.

The liners may be formed from any suitable thermoset polymer or thermoplastic polymer. The polymer material may have a low to medium coefficient of friction of about 0.12 to about 0.27, a wear factor no less than about 1.20 E-14 m2/N, a tensile strength of about 4400 to about 12400 psi, a coefficient of linear thermal expansion of about 3.3 to about 7.2 10^-5/F, and a water absorption (50% RH) in a range of about 0.07% to about 0.22%. As one example, the liners may be formed from an unreinforced, semi-crystalline thermoplastic polyester based on polyethylene terephthalate (PET-P), for example, ERTALYTE®. As another example, the liners may be formed from a compression molded ultra high molecular weight polyethylene (UHMW-PE), or an extruded UHMW-PE. As another example, the liners may be formed from an injection molded acetal homopolymer, for example Delrin® 100P. Other suitable polymeric materials include polyolefins (for example, HDPE, LDPE, polypropylene), polyesters (for example, PET, PBT), acetals (for example, Delrin), polyamides (for example, Nylon), fluorinated polymers (for example, PTFE, PFA, FEP, PVDF, ETFE), vinyls (for example, PVC), acrylics (for example, PMMA), polycarbonates, polyimides (for example, PEI), polysulphones (for example, PES), among others, and blends and alloys thereof. The liners may be made by means of injection molding, machining, compression molding and/or extruding. In some applications, the liners may be made by means of additive manufacturing.

Figure 9:
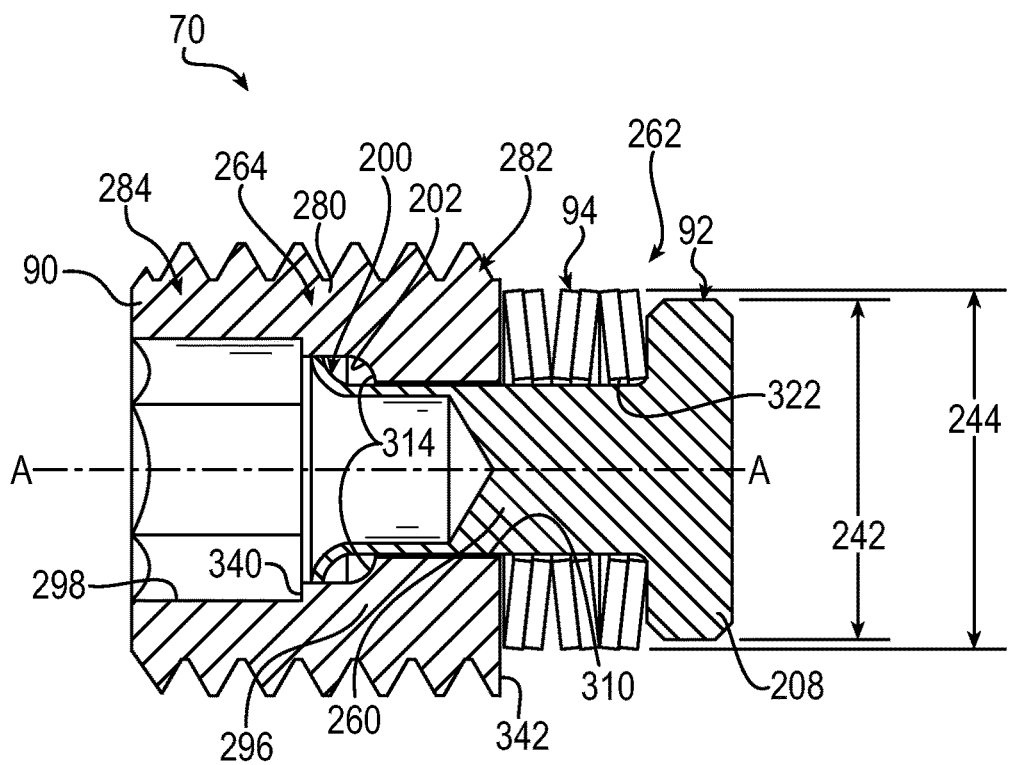
FIG. 9 is a cross-section view of the brake actuator of FIG. 8 as viewed from the plane 9-9 in FIG. 8.

Referring to FIGS. 3 and 9, the inner or minor diameter 240 of the threaded opening 206 in the hub 28 is greater than a maximum width 242 of the plunger 92 in axial cross section and a maximum width 244 of the spring 94 in axial cross section. In the illustrative embodiment, the plunger 92 and spring 94 are circular in axial cross section and therefore their maximum widths 242, 244 represent outer diameters 242, 244. As will be appreciated, this, in conjunction with the self-contained structure of the brake actuator 70, simplifies assembly and field service since the components need not be separately handled and positioned and/or aligned relative to one another, and the brake actuator 70 can be inserted into the threaded opening 206 and adjustably mounted in the hub 28 with the cap 90, plunger 92, and spring 94 responding in cooperative relationship to one another.

FIG. 3 shows the head 208 of the plunger 92 exerting a force against the rear of the tab 182 when the brake actuator 70 applies the frictional braking force to the clamp portions 30, 32 to lock the extension arm 16 to the central shaft 14. The rear of the tab 182 has a larger surface area than the head 208 of the plunger 92. This allows the rear of the tab 182 to slide relative to the head 208 of the plunger 92 in a direction axially and radially relative to the central shaft 14. The head 208 of the plunger 92 does not require any particular alignment with the rear of the tab 182 apart from the abutting relationship therebetween. This is unlike some conventional brake actuators in which a distal end of a plunger must be aligned with and slidably inserted into a hole in the tab of the respective clamp portion, confining assembly and operating motion of the tab to that of the brake actuator and vice versa. As will be appreciated from the present embodiment, when the brake actuator 70 urges the tabs 180, 182 together to urge the clamp portions 30, 32 closer together, the clamp portions 30, 32 may shift axially and radially relative to the central shaft 14 to a position that is more centered and aligned with respect to the central shaft 14. As such, the tabs 180, 182 of the clamp portions 30, 32 will also shift. The abutting slidable relationship between the tabs 180, 182 and the respective wall 218 of the notch 186 and the head 208 of the plunger 92 can enable such shifting, and thus enable the clamp portions 30, 32 to be self-centering and self-aligning relative to the central shaft 14. This also allows for a built-in concentricity clearance between the hub 28 and the brake clamp assembly 18, particularly over repeated angular adjustments of the extension arm 16 relative to the central shaft 14.

FIGS. 8-12 show greater details of the brake actuator 70 of the medical device support system 10. The illustrative brake actuator 70 includes the cap 90, the plunger 92, and the spring 94, coupled together as a self-contained assembly. The plunger 92 includes a rod 260 and a head 208. The head 208 is at one axial end 262 of the rod 260, and a stop flange 200 is at an opposite axial end 264 of the rod 260. The cap 90 includes a body 280, and a mating coupling 296 at one axial end 282 of the body 280, and a driving end 298 at an opposite axial end 284 of the body 280. The mating coupling 296 is coupled to the rod 260 for reciprocable axial movement relative to the rod 260 toward and away from the head 208. The stop flange 200 is configured to abut an interior portion 202 of the mating coupling 296 to prevent separation of the plunger 92 from the cap 90. The spring 94 is disposed between the mating coupling 296 and the head 208, and configured to exert a biasing force against movement of the cap 90 axially toward the head 208.

The cap 90 can be circular in axial cross section and the outer diameter of the cap 90 may be greater than the maximum width 242 of the head 208 in axial cross section and the maximum width 244 of the spring 94 in axial cross section. This enables the brake actuator 70 including its components 90, 92, 94 to pass through the threaded opening 206 in the hub 28. In the illustrative embodiment, the plunger 92 and spring 94 are circular in axial cross section and therefore their maximum widths 242, 244 represent outer diameters 242, 244. The cap 90 can be externally threaded for threadable engagement with the internal thread of the threaded opening 206 in the hub 28, as shown in FIG. 3. In one form, the inner or minor diameter of the thread of the cap 90 is greater than the outer diameters 242, 244 of the respective plunger 92 and spring 94. As described above with respect to the minor diameter of the threaded opening 206 of the hub, this enables the brake actuator 70 including its components 90, 92, 94 to be inserted into the threaded opening 206 and adjustably mounted in the hub 28 as a self-contained assembly, thereby simplifying assembly and field service of the medical device support system 10.

Figure 10:
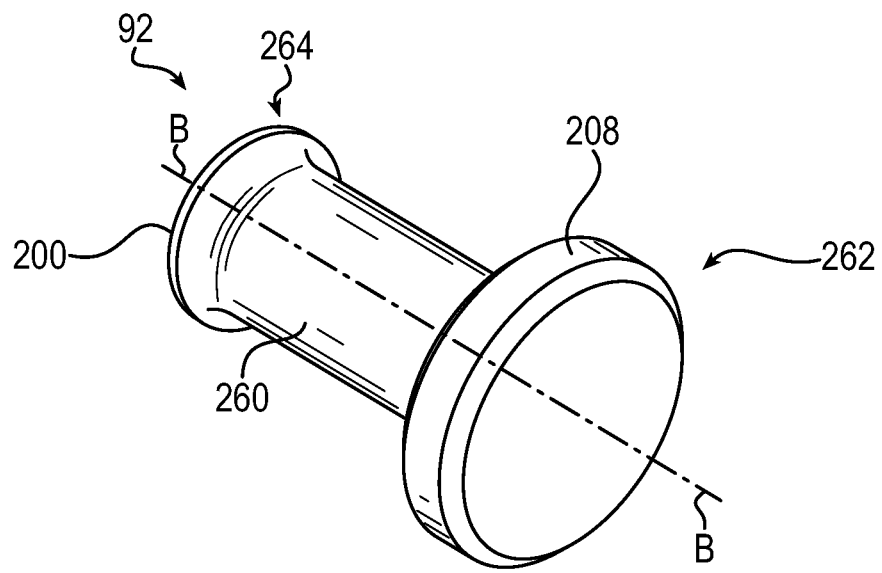
FIG. 10 is a perspective view of a plunger of the FIG. 8 brake actuator.

As shown in FIG. 9, the end 264 of the plunger rod 260 has a hollow rod end, and the stop flange 200 of the plunger 92 is formed as a flared end of the hollow rod end. The cap 90 has a central opening 310 that slidably receives the rod 260 to guide the reciprocable axial movement of the plunger 92. As shown in FIGS. 9 and 10, the stop flange 200 may project radially outward from the rod 260, and the interior portion 202 of the mating coupling 296 may include a ledge 314 that projects radially outward from the central opening 310. The stop flange 200 abuts the ledge 314 to prevent separation of the plunger 92 from the cap 90. In the illustrative embodiment, the stop flange 200 is annular in shape and the radially outward projecting ledge 314 is annular in shape.

Figure 11:
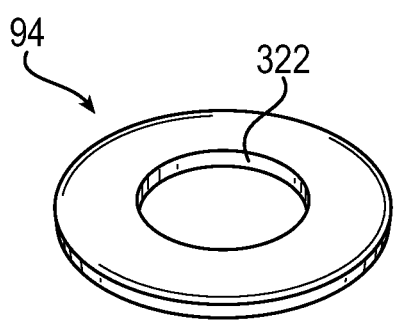
FIG. 11 is a perspective view of a spring of the FIG. 8 brake actuator.
Figure 12:
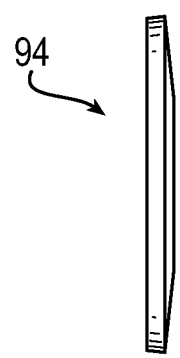
FIG. 12 is a side view of the FIG. 11 spring.

The spring 94 can include any suitable means for exerting a biasing force against movement of the cap 90 axially toward the plunger 92, in the illustrative embodiment the rear of the plunger head 208. FIG. 9 shows an example in which the spring 94 is in the form of a plurality of Belleville washers, one of which is shown in FIGS. 11 and 12. As shown in FIG. 9, the Belleville washers can be stacked in parallel and/or series. The Belleville washers allow flexibility in creating a desired spring constant and deflection capacity, and hence stiffness. Referring to FIGS. 9 and 8, the inner diameter 322 of the Belleville washer spring 94 is slightly larger than the outer diameter of the rod 260 of the plunger 92, thereby aiding in the reciprocable axial movement of the plunger 92 relative to the spring 94.

The driving end 298 of the cap 90 includes a tool fitting for mating with a tool from which the cap 90 can be driven axially by threadably engaging the threaded opening 206 in the hub 28 of the medical device support system 10. The tool fitting can be adapted to accommodate any tool for example a keystone tip screwdriver, Phillips tip screwdriver, hexagonal wrench, open-end wrench, offset wrench, or ratchet wrench. For example, the tool fitting may be a hexagonal fitting as shown in FIG. 8, or a keystone groove, a crossed groove, or polygonal groove, among others. Further, instead of the aforesaid hexagonal groove, keystone groove, crossed groove, or polygonal groove, a hexagonal rib, keystone rib, crossed rib, or key rib may be made on and raised from the top wall of the driving end 298 to fit a respective matching wrench tool.

One way to manufacture the brake actuator 70 is to insert the plunger 92, pre-flared, through the central opening 322 of the spring 94 and through the central opening 310 of the cap 90, to a position at which the end 264 of the plunger 92 extends beyond the ledge 314 of the interior portion 202 of the cap 90. The end 264 can then be flared to form the stop flange 200 of the plunger 92, thereby coupling the plunger 92 to the cap 90 with the spring 94 disposed therebetween. The cap 90 may be manufactured, for example, by starting with a socket set screw having a hexagonal fitting as shown in FIG. 8 and, prior to installing the plunger 92, drilling a through hole therethrough from the base 340 of the hexagonal fitting to the spring facing end 342 of the cap 90, thereby forming the central opening 310 of the cap 90. The interior portion 202 of the cap 90 can be formed for example by counterboring from the base 340 of the hexagonal fitting to a suitable distance therefrom, thereby forming the ledge 314 of the interior portion 202, to accommodate the flared end 202 of the plunger 92.

Figure 13:
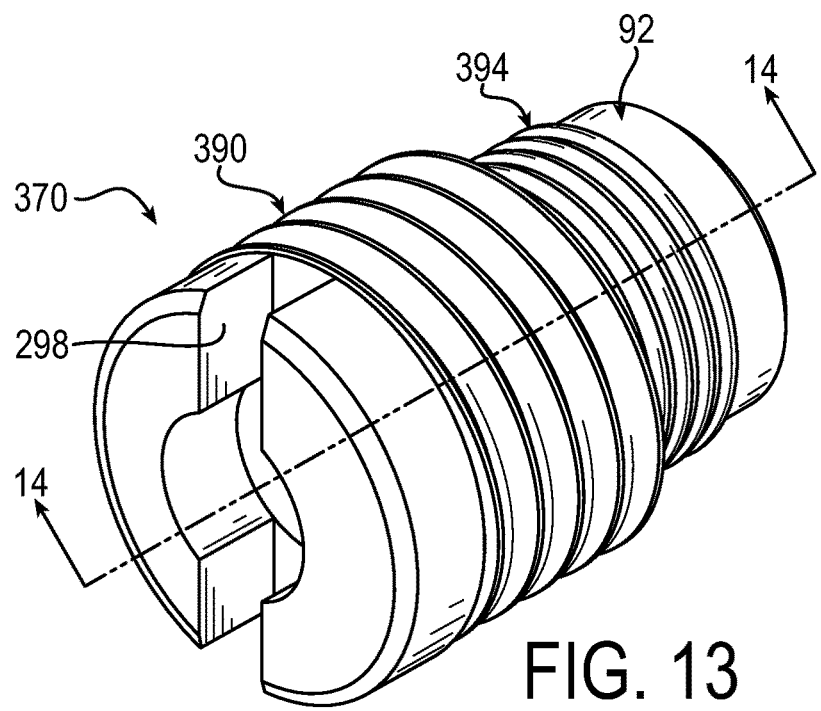
FIG. 13 is a perspective view of a brake actuator in accordance with an embodiment of the invention.
Figure 14:
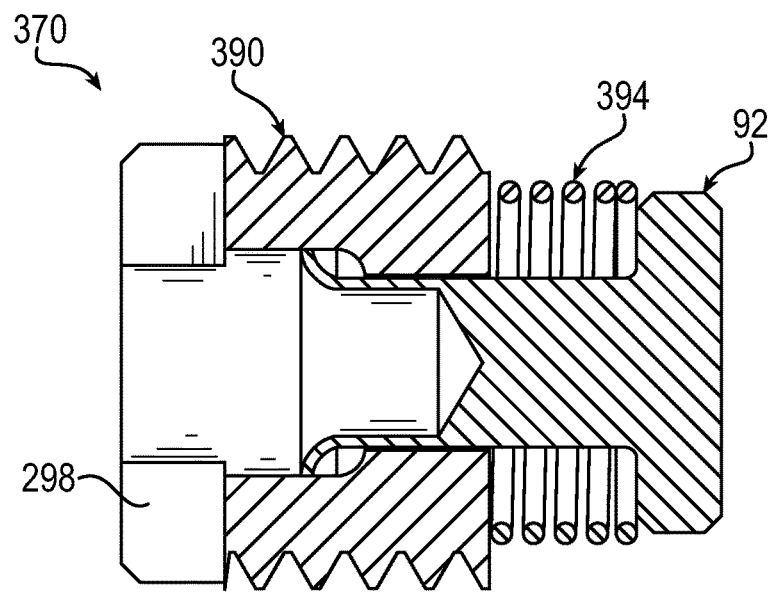
FIG. 14 is a cross-section view of the brake actuator of FIG. 13 as viewed from the plane 14-14 in FIG. 13.

FIGS. 13 and 14 show a brake actuator 370 in accordance with another embodiment of the invention. The brake actuator 370 in FIGS. 13 and 14 is in many respects similar to the above-referenced FIGS. 8-12 brake actuator 70, and consequently the same reference numerals are used to denote structures corresponding to similar structures in the FIGS. 8-12 brake actuator 70. In addition, the foregoing description of the FIGS. 8-12 brake actuator 70 is equally applicable to the brake actuator 370 in FIGS. 13-14 except as noted below. Moreover, it will be appreciated upon reading and understanding the specification that aspects of the brake actuators 70, 370 may be substituted for one another or used in conjunction with one another where applicable. The brake actuator 370 has a spring 394 in the form of a coil spring 394, and a cap 390 that has a driving end 298 that includes a tool fitting for mating with a flat tip screwdriver. The plunger 92 can be coupled to the cap 390 in a manner similar to that described above with respect to the plunger 92 and cap 90.

Figure 15:
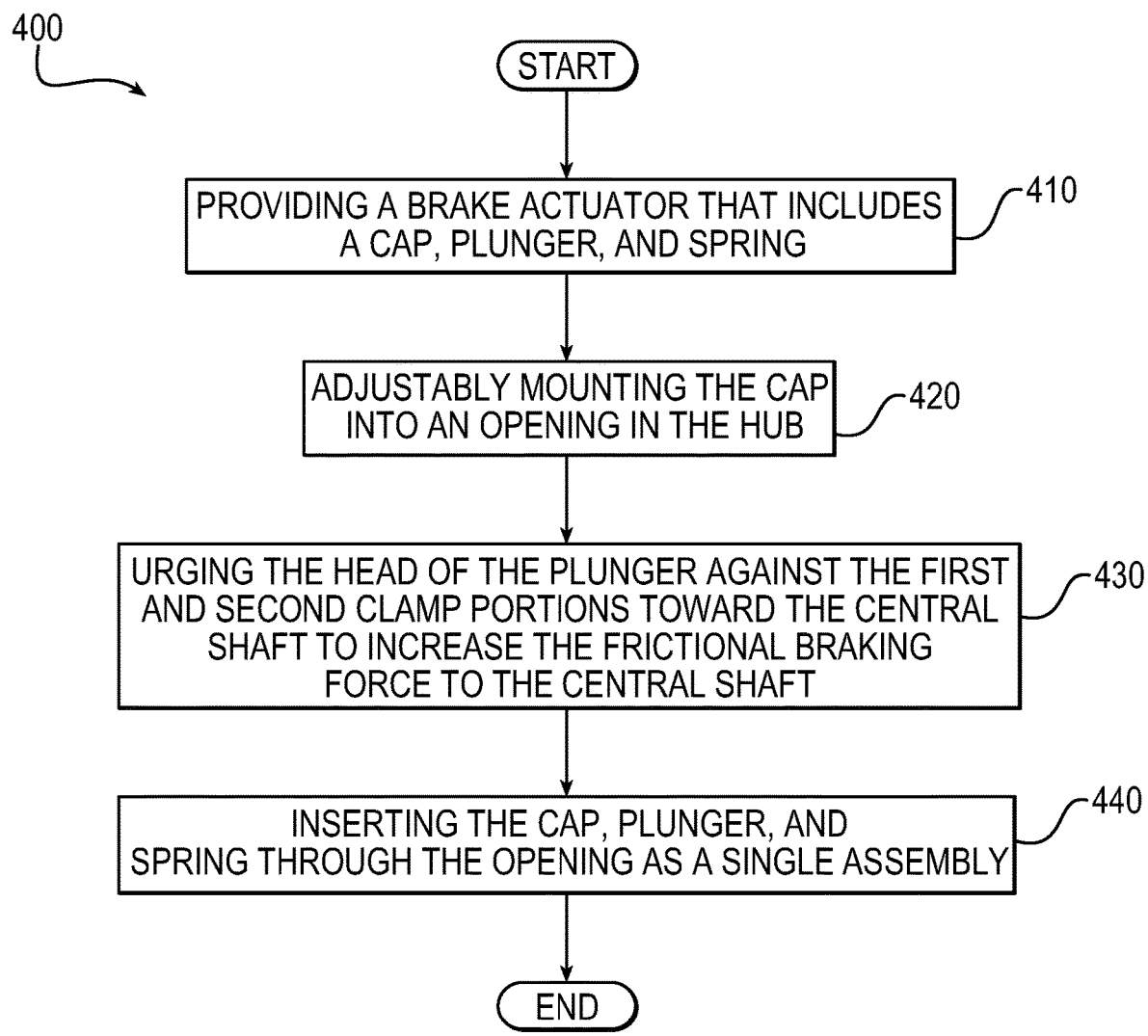
FIG. 15 shows a flowchart of a method of installing a brake actuator in a medical device support system in accordance with an embodiment of the invention.

Referring now to FIG. 15, there is shown a flowchart 400 of a method of installing a brake actuator in a medical device support system in accordance with the invention, such as the brake actuator 70 in the medical device support system 10 of FIG. 1. At step 410, a brake actuator 70 is provided that includes a cap 90, a plunger 92 coupled to the cap 90 for reciprocable axial movement relative to the cap 90, and a spring 94 disposed between the cap 90 and the plunger 92 to exert a biasing force against movement of the cap 90 axially toward the plunger 92. At step 420, the cap 90 is adjustably mounted into the opening 206 in the hub 28 and the cap 90 is coupled to the plunger 92 to urge the first and second clamp portions 30, 32 toward the central shaft 14 to increase a frictional braking force to the central shaft 14. At step 430, as the cap 90 is adjustably mounted into the opening 206, the cap 90, against the biasing force of the spring 94, urges the spring 94 against the head 208 of the plunger 92, and the head 208 of the plunger 92, in turn, urges the first and second clamp portions 30, 32 toward the central shaft 14 to increase the frictional braking force to the central shaft 14. At step 440, as the cap 90 is mounted into the opening 206, the cap 90 pushes the plunger 92, and the spring 94 disposed between the plunger 92 and the cap 90, through the opening 206 as a self-contained assembly.

In an embodiment, the cap 90 can be removed from the opening 206 in the hub 28, and as the cap 90 is removed the cap 90 pulls the plunger 92, as well as the spring 94 disposed between the plunger 92 and the cap 90, through the opening 206 as a self-contained assembly.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A medical device support system comprising:
   a central shaft;
   an extension arm having a support for a medical device and a hub at its proximal end mounted to the central shaft for pivotable movement about the central shaft;
   a brake clamp assembly secured in the hub for rotation therewith and including first and second clamp portions; and,
   a brake actuator including a cap, a plunger coupled to the cap for reciprocable axial movement relative to the cap, and a spring disposed between the cap and the plunger and configured to exert a biasing force against movement of the cap axially toward the plunger,
   wherein the cap is adjustably mounted to the hub and coupled to the plunger to selectively urge the first and second clamp portions either toward or away from the central shaft to respectively increase or decrease a frictional braking force to the central shaft.

2. The medical device support system of claim 1, wherein the plunger is coupled to the cap to prevent separation of the plunger from the cap.

3. The medical device support system of claim 1, wherein the cap is configured to compress the spring against a head of the plunger, and the head of the plunger, in turn, urges the first and second clamp portions toward the central shaft to increase the frictional braking force to the central shaft.

4. The medical device support system of claim 1, wherein the cap threadably engages a threaded opening in the hub.

5. The medical device support system of claim 4, wherein the minor diameter of the threaded opening in the hub is greater than a maximum width of the plunger in axial cross section and a maximum width of the spring in axial cross section.

6. The medical device support system of claim 1, wherein the brake clamp assembly is configured to operate in a passive manner, preventing motion of the extension arm relative to the central shaft by means of the frictional braking force, wherein the frictional braking force can be overcome by a user pushing on the extension arm.

7. The medical device support system of claim 1, wherein the first and second clamp portions form a split collar around the central shaft, and free ends of the clamp portions include respective tabs that protrude radially outwardly relative to the central shaft, and wherein the cap is adjustably mounted to the hub and coupled to the plunger to exert a force on the plunger against one of the tabs to apply a compressive force to the tabs to urge the first and second clamp portions toward one another thereby to impart the frictional braking force to the central shaft.

8. The medical device support system of claim 1, wherein a head of the plunger exerts the force against one of a plurality of tabs, and one of the plurality of tabs is slidable relative to the head in a direction axially and radially relative to the central shaft.

9. The medical device support system of claim 1, wherein the medical device is a surgical light.

10. The medical device support system of claim 1, wherein the brake clamp assembly includes brake liners made of a material selected from polyolefins, polyesters, acetals, polyamides, fluorinated polymers, vinyls, acrylics, polycarbonates, polyimides, polysulphones, and blends and alloys thereof.

11. The medical device support system of claim 1, wherein the brake clamp assembly includes brake liners made of a material including unreinforced, semi-crystalline thermoplastic polyester based on polyethylene terephthalate (PET-P).

12. The medical device support system of claim 1, wherein the brake clamp assembly includes brake liners made of a material including UHMW-PE.

13. A brake actuator for a medical device support system, the brake actuator comprising:
    a plunger including a rod, a head at one axial end of the rod, and a stop flange at an opposite axial end of the rod;
    a cap including a body, a mating coupling at one axial end of the body, and a driving end at an opposite axial end of the body, wherein the mating coupling is coupled to the rod for reciprocable axial movement relative to the rod toward and away from the head, and wherein the stop flange is configured to abut an interior portion of the mating coupling to prevent separation of the plunger from the cap; and
    a spring disposed between the mating coupling and the head, and configured to exert a biasing force against movement of the cap axially toward the head.

14. The brake actuator of claim 13, wherein the cap is externally threaded and has a minor diameter that is greater than a maximum width of the head in axial cross section and a maximum width of the spring in axial cross section.

15. The brake actuator of claim 13, wherein the opposite axial end of the rod has a hollow rod end, and the stop flange is formed as a flared end of the hollow rod end.

16. The brake actuator of claim 13, wherein the cap has a central opening that slidably receives the rod to guide the reciprocable axial movement.

17. The brake actuator of claim 16, wherein the stop flange projects radially outward from the rod, and the interior portion of the mating coupling includes a ledge that projects radially outward from the central opening, and the stop flange abuts the ledge to prevent separation of the plunger from the cap.

18. The brake actuator of claim 17, wherein the stop flange is annular in shape and the radially outward projecting ledge is annular in shape.

19. The brake actuator of claim 13, wherein an inner diameter of the spring is slightly larger than an outer diameter of the rod.

20. The brake actuator of claim 13, wherein the spring includes a plurality of Belleville washers.

21. The brake actuator of claim 13, wherein the cap is externally threaded and wherein the driving end of the cap includes a tool fitting for mating with a tool from which the cap can be driven axially by threadably engaging a threaded opening in a hub of the medical device support system.

22. A method of adjusting a brake assembly of a medical device support system having a central shaft, an extension arm having a support for a medical device and a hub at its proximal end mounted to the central shaft for pivotable movement about the central shaft, and a brake clamp assembly secured in the hub for rotation therewith and including first and second clamp portions, the method comprising:

providing a brake actuator including a cap, a plunger coupled to the cap for reciprocable axial movement relative to the cap, and a spring disposed between the cap and the plunger to exert a biasing force against movement of the cap axially toward the plunger;

adjustably mounting the cap into an opening in the hub and coupling the cap to the plunger to urge the first and second clamp portions toward the central shaft to increase a frictional braking force to the central shaft, wherein as the cap is adjustably mounted into the opening the cap, against the biasing force of the spring, urges the spring against a head of the plunger, and the head of the plunger, in turn, urges the first and second clamp portions toward the central shaft to increase a frictional braking force to the central shaft;

wherein as the cap is mounted into the opening the cap pushes the plunger, and the spring disposed between the plunger and the cap, through the opening as a self-contained assembly.

23. The method of claim 22, further comprising removing the cap from the opening in the hub, wherein as the cap is removed the cap pulls the plunger, and the spring disposed between the plunger and the cap, through the opening as a self-contained assembly.

\* \* \* \* \*